United States Patent [19]

Markert et al.

[11] Patent Number: 4,522,646
[45] Date of Patent: Jun. 11, 1985

[54] 3,7-DICHLOROQUINOLINE DERIVATIVES AND THEIR USE FOR CONTROLLING UNDESIRABLE PLANT GROWTH

[75] Inventors: Jürgen Markert, Mutterstadt; Helmut Hagen, Frankenthal; Bruno Wuerzer, Otterstadt, all of Fed. Rep. of Germany

[73] Assignee: BASF Aktiengesellschaft, Fed. Rep. of Germany

[21] Appl. No.: 507,109

[22] Filed: Jun. 23, 1983

[30] Foreign Application Priority Data

Jun. 26, 1982 [DE] Fed. Rep. of Germany ....... 3223884

[51] Int. Cl.$^3$ ................. A01N 9/22; C07D 215/14; C07D 401/12; C07D 405/12
[52] U.S. Cl. .............................. 71/94; 71/90; 71/92; 544/363; 544/405; 546/174; 546/175
[58] Field of Search ............... 546/174, 175; 544/405, 544/363; 71/90, 92, 94

[56] References Cited

U.S. PATENT DOCUMENTS 2,661,276 12/1953 Schlesinger et al. ............... 71/2.5
3,624,091 11/1971 Daum et al. .......................... 546/174
3,813,399 5/1974 Huber-Emden et al. ........... 546/174

FOREIGN PATENT DOCUMENTS 943962 3/1974 Canada ............................. 546/174
1424359 2/1976 United Kingdom .

Primary Examiner—Glennon H. Hollrah
Assistant Examiner—James H. Turnipseed
Attorney, Agent, or Firm—Keil & Weinkauf

[57] ABSTRACT 3,7-dichloroquinoline derivatives of the formula

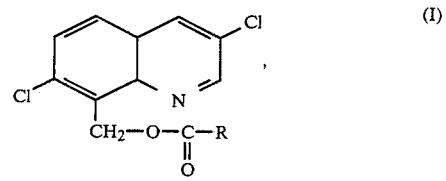

where R has the meanings given in the disclosure, a process for the preparation thereof, and their use for combating unwanted plant growth.

9 Claims, No Drawings

3,7-DICHLOROQUINOLINE DERIVATIVES AND THEIR USE FOR CONTROLLING UNDESIRABLE PLANT GROWTH

The present invention relates to 3,7-dichloroquinoline derivatives, herbicides which contain these compounds as active ingredients and a method of controlling undesirable plant growth using these active ingredients.

Quinoline derivatives having weak herbicidal properties have been disclosed in German Laid-Open application No. DOS, 2,322,143 and U.S. Pat. No. 2,661,276.

We have found that 3,7-dichloroquinoline derivatives of the formula

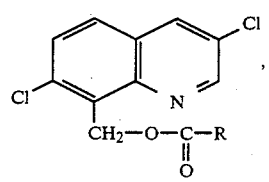

where R is hydrogen, $C_1-C_8$-alkyl, $C_2-C_6$-alkenyl, $C_1-C_6$-hydroxyalkyl, cyclohexyl, or phenyl which is unsubstituted or monosubstituted or polysubstituted by nitro, cyano, benzoyl, hydroxyl, methyl, methoxy, halogen, trihalomethyl, amino or dialkylamino, or is pyridyl, piperazinyl, pyrazinyl, piperidinyl, thienyl, furyl, thiazolidinyl, carboxyl, trihalomethyl, unsubstituted or substituted benzyl, benzophenonyl, phenoxymethyl or anilinomethyl, have a substantial selective herbicidal action.

In formula I, R can be, for example, hydrogen, straight-chain or branched $C_1-C_8$-alkyl, e.g. methyl, ethyl, n-propyl, n-butyl, i-butyl, n-pentyl, n-hexyl or n-octyl, straight-chain or branched $C_2-C_6$-alkenyl, e.g. allyl or propenyl, straight-chain or branched $C_1-C_6$-hydroxyalkyl, e.g. hydroxymethyl, 1-hydroxyethyl, 2-hydroxyethyl, 1-hydroxyisopropyl, 3-hydroxy-n-propyl or 1-hydroxy-3-methyl-n-butyl, phenyl which is unsubstituted or monosubstituted or polysubstituted by nitro, cyano, benzoyl, hydroxyl, methyl, methoxy, halogen, such as chlorine, fluorine, bromine or iodine, trihalomethyl, such as trifluoromethyl or trichloromethyl, amino or dialkylamino where each alkyl is of 1 to 4 carbon atoms, such as dimethylamino or diethylamino, or is pyridyl, piperazinyl, pyrazinyl, piperidinyl, thienyl, furyl, thiazolidinyl, carboxyl, trihalomethyl, e.g. trifluoromethyl or trichloromethyl, or is benzophenonyl, phenoxymethyl, anilinomethyl or benzyl which is unsubstituted or substituted by $C_1-C_4$-alkyl, such as methyl or ethyl. In formula I, R is preferably $C_1-C_8$-alkyl, in particular $C_1-C_4$-alkyl, e.g. methyl.

The compounds of the formula I are obtained in a conventional manner by reacting 3,7-dichloro-8-chloromethylquinoline with an equimolar amount or up to twice the equimolar amount of a carboxylate of the formula

where R has the above meanings and $M^{\oplus}$ is an alkali metal ion, e.g. lithium, sodium or potassium.

The reaction is carried out at from 80° to 100° C. in an inert solvent, such as dimethylformamide, dimethylsulfoxide, an alcohol, e.g. ethanol or methylglycol, or water. It is complete after from 2 to 6 hours. The reaction is carried out at from 80° to 100° C.

In this process, the carboxylate of the formula II is either prepared in the particular reaction medium using the calculated amount of base, e.g. sodium methylate, potassium ethylate, potassium hydroxide, sodium hydroxide, sodium carbonate or sodium ethylate, or is first isolated and then added as a salt.

3,7-Dichloro-8-chloromethylquinoline can be prepared by chlorinating 7-chloro-8-methylquinoline in dichlorobenzene at from 140° to 160° C. Under suitable conditions, side chain chlorination is accompanied by selective chlorination at the 3-position of the quinoline nucleus.

EXAMPLE 1

89 parts by weight of 7-chloro-8-methylquinoline and 0.5 part by weight of azobisisobutyronitrile in 500 parts by weight of dichlorobenzene are heated to 140° C., and 80 parts by weight of chlorine are passed in, beginning at this temperature. During the passage of chlorine, the temperature is increased to 160° C. After the addition of chlorine is complete, the solution is flushed with nitrogen, the major part of the solvent is distilled off and the precipitated solid is filtered off under suction and washed with petroleum ether. 113 parts by weight (93% of theory) of 3,7-dichloro-8-chloromethylquinoline of melting point 129° C. are obtained.

24.5 parts by weight of 3,7-dichloro-8-chloromethylquinoline and 13 parts by weight of sodium formate in 220 parts by weight of dimethylsulfoxide are heated for 6 hours at 100° C. The mixture is then cooled, water is added and the precipitated product is filtered off under suction and recrystallized from toluene. 21.5 parts by weight (84% of theory) of 3,7-dichloro-8-formyloxymethylquinoline of melting point 146° C. are obtained.

EXAMPLE 2

16 parts by weight of nonanecarboxylic acid, 20 parts by weight of 30% strength sodium methylate solution and 440 parts by weight of dimethylsulfoxide are stirred for 1 hour at 100° C. Thereafter, 24.5 parts by weight of 3,7-dichloro-8-chloromethylquinoline are introduced and the reaction mixture is stirred for a further 2 hours at 100° C. The reaction solution is then cooled, water is added and the precipitated solid is filtered off under suction and recrystallized from toluene. 32.5 parts by weight (89% of theory) of 3,7-dichloro-8-octylcarbonyloxymethylquinoline of melting point 92° C. are obtained.

EXAMPLE 3

33 parts by weight of 2-nitrobenzoic acid, 40 parts by weight of 30% strength sodium methylate solution and 440 parts by weight of dimethylsulfoxide are stirred for 2 hours at 100° C. Thereafter, 49 parts by weight of 3,7-dichloro-8-chloromethylquinoline are introduced and the reaction mixture is stirred for a further 2 hours at 100° C. The solution is then cooled, water is added and the precipitated solid is filtered off under suction and recrystallized from toluene. 69 parts by weight (92% of theory) of 3,7-dichloro-8-[(2-nitrophenyl)-carbonyloxymethyl]-quinoline of melting point 152° C. are obtained.

For example the following compounds of the formula I may be prepared analogously:

| Compound no. | R | Melting point °C. |
|---|---|---|
| 4 | CH$_3$ | 144 |
| 5 | C$_2$H$_5$ | 140 |
| 6 | phenyl | 184 |
| 7 | 4-chlorophenyl | |
| 8 | pyrid-3-yl | 177 |
| 9 | CCl$_3$ | |
| 10 | CF$_3$ | |
| 11 | benzyl | 142 |
| 12 | cyclohexyl | 156 |
| 13 | phenoxymethyl | 126 |
| 14 | anilinomethyl | 105 |
| 15 | prop-1-enyl | 112 |
| 16 | 3,4,5-trimethyl-phenyl | |
| 17 | tert.-C$_4$H$_9$ | 110 |
| 18 | thien-3-yl | |
| 19 | thien-2-yl | |
| 20 | n-C$_3$H$_7$ | |
| 21 | n-C$_4$H$_9$ | |
| 22 | n-C$_5$H$_{11}$ | |
| 23 | 2-chlorophenyl | 165 |
| 24 | piperid-4-yl | |
| 25 | 4-methoxyphenyl | 197 |
| 26 | 2-amino-phenyl | 169 |
| 27 | fur-3-yl | |
| 28 | fur-2-yl | |
| 29 | 4-methylphenyl | 184 |
| 30 | (2-methylphenyl)-C(=O)-(4-methylphenyl) | 128 |
| 31 | piperazin-2-yl | |
| 32 | 3,4,5-trihydroxyphenyl | |
| 33 | pyrid-4-yl | |
| 34 | pyrid-2-yl | |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient. Application rates are from 0.1 to 10 kg of active ingredient per hectare.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 4 is dissolved in a mixture consisting of 25 parts by weight of cyclohexanol, 65 parts by weight of a mineral oil fraction having a boiling point between 210° and 280° C. and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 8 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 4 is intimately mixed with 97 parts by weight of particulate kaolin. A dust is obtained containing 3% by weight of the active ingredient.

VII. 30 parts by weight of compound no. 17 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 13 is intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 68 parts of a paraffinic mineral oil. A stable oily dispersion is obtained.

The active ingredients or agents may be applied preor postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated, and the growth stage of the plants, and varies from 0.1 to 5 kg/ha and more, but is preferably from 0.05 to 4 kg/ha.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate varied for example from 2.0 to 4.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The rice plants used for the postemergence treatment were grown in a peat-enriched substrate to ensure better growth than is possible in a sandy loam. For this treatment, either plants which had been sown directly in the pots and grown there were selected, or plants which had been grown separately as seedlings and transplanted to the experiment vessels a few days before treatment. No covers were placed on the pots in this treatment method. The application rate for postemergence treatment was, for example, 2.0 kg of active ingredient per hectare.

The pots were set up in the greenhouse—species from warmer areas at from 20° to 35° C., and species from moderate climates at 10° to 25° C. The experiments were run for up to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the greenhouse experiments were *Allium cepa,* Amaranthus spp., *Beta vulgaris, Brassica napus, Cassia tora, Euphorbia geniculata, Echinochloa crus-galli,* Ipomoea spp., *Galium aparine, Oryza sativa, Sesbania exaltata, Solanum nigrum,* and *Triticum aestivum.*

In the experiments, for example compound no. 4, applied pre- and postemergence at a rate of 2.0 kg/ha, had a herbicidal action on unwanted broadleaved and grassy plants, and was well tolerated by crop plants, e.g., rape, rice, onions and wheat. Compounds nos. 1 and 8, for instance, selectively combated unwanted plants in rape and sugarbeets on preemergence application of 2.0 to 4.0 kg/ha. Compounds nos. 2, 5, 13 and 17, also applied preemergence at a rate of 2.0 kg/ha, had a significant action on unwanted plants and were selective in agricultural crops such as beets and rape.

In view of the good tolerance of the herbicides according to the invention, or agents containing them, by numerous broadleaved and other crops, and the numerous application methods possible, they may be used in a large number of crops for removing unwanted plant growth.

The following crops may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |

| Botanical name | Common name |
| --- | --- |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* | parsley |
| spp. tuberosum | |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the compounds according to the invention may be mixed and applied together with numerous representatives of other herbicidal or growth-regulating active ingredient groups. Examples of suitable mixture components are diazines. 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds, either on their own or combined with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A 3,7-dichloroquinoline derivative of the formula

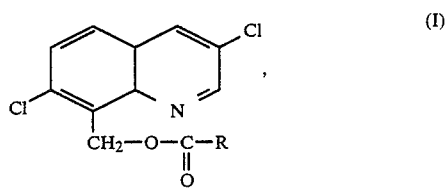

where R is hydrogen, $C_1$–$C_8$-alkyl, $C_2$–$C_6$-alkenyl, $C_1$–$C_6$-hydroxyalkyl, cyclohexyl, or phenyl which is unsubstituted or monosubstituted by nitro, cyano, benzoyl, hydroxyl, methyl, methoxy, halogen, trihalomethyl, amino or dialkylamino where each alkyl is of 1–4 carbons, or is pyridyl, piperazinyl, pyrazinyl, trihalomethyl, unsubstituted benzyl or benzyl substituted by $C_1$–$C_4$ alkyl, benzophenonyl, phenoxymethyl or anilinomethyl.

2. A 3,7-dichloroquinoline derivative of the formula I as claimed in claim 1, where R is $C_1$–$C_8$-alkyl.

3. 3,7-Dichloro-8-methylcarbonyloxymethylquinoline.

4. A herbicide containing inert additives and a herbicidally effective amount of a 3,7-dichloroquinoline derivative of the formula I as claimed in claim 1.

5. A herbicide containing inert additives and from 0.1 to 95 wt % of a 3,7-dichloroquinoline derivative of the formula I as claimed in claim 1.

6. A herbicide containing inert additives and a herbicidally effective amount of a 3,7-dichloroquinoline derivative of the formula I as claimed in claim 1, R denoting $C_1$–$C_8$-alkyl.

7. A herbicide containing inert additives and a herbicidally effective amount of 3,7-dichloro-8-methylcarbonyloxymethylquinoline.

8. A process for combating the growth of unwanted plants, wherein the plants or their location are treated with a herbicidally effective amount of a 3,7-dichloroquinoline derivative of the formula I as claimed in claim 1.

9. A 3,7-dichloroquinoline derivative of the formula I as defined in claim 1, where R is hydrogen, $C_1$–$C_8$-alkyl, $C_2$–$C_6$-alkenyl, cyclohexyl, or phenyl which is unsubstituted or monosubstituted by nitro, benzoyl, methyl, methoxy, halogen, or amino or is pyridyl, benzyl, benzophenonyl, phenoxymethyl or anilinomethyl.

* * * * *